United States Patent [19]

Duggan et al.

[11] Patent Number: 4,857,546

[45] Date of Patent: Aug. 15, 1989

[54] NOVEL HMG-COA REDUCTASE INHIBITORS

[75] Inventors: Mark Duggan, Wynnewood; George D. Hartman, Lansdale, both of Pa.

[73] Assignee: Merck & Co., Inc., Rahway, N.J.

[21] Appl. No.: 142,378

[22] Filed: Jan. 7, 1988

[51] Int. Cl.$^4$ .................. A61K 31/365; C07D 309/30
[52] U.S. Cl. ..................... 514/460; 549/292; 544/60; 544/59; 544/149; 544/162; 544/359; 544/389; 546/207; 546/245; 548/518; 548/531
[58] Field of Search ............... 514/460, 510; 549/292; 560/119

[56] References Cited

U.S. PATENT DOCUMENTS 4,444,784  4/1984  Hoffman et al. .................. 549/292
4,661,483  4/1987  Hoffman et al. .................. 549/292

Primary Examiner—Glennon H. Hollrah
Assistant Examiner—Ba Trinh
Attorney, Agent, or Firm—Melvin Winokur; Joseph F. DiPrima

[57] ABSTRACT

Novel 3-hydroxy-3-methylglutarylcoenzyme A (HMG-CoA) reductase inhibitors are useful as antihypercholesterolemic agents and are represented by the following general structural formulae (I) and (II):

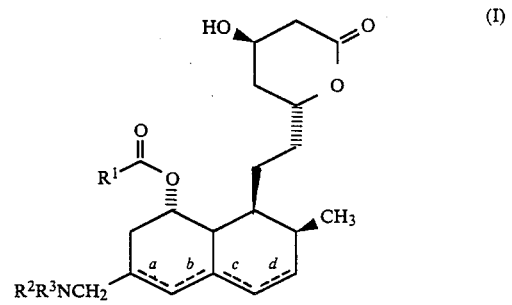

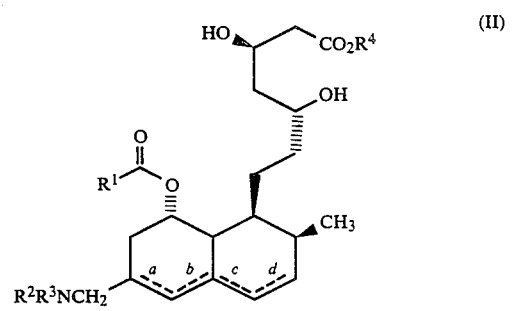

19 Claims, No Drawings

NOVEL HMG-COA REDUCTASE INHIBITORS

BACKGROUND OF THE INVENTION

Hypercholesterolemia is known to be one of the prime risk factors for atherosclerosis and coronary heart disease, the leading cause of death and disability in Western countries. The bile acid sequestrants seem to be moderately effective but they must be consumed in large quantities, i.e., several grams at a time, and they are not very palatable.

There are agents known, however, that are very active antihypercholesterolemic agents which function by limiting cholesterol biosynthesis via inhibiting the enzyme, HMG-CoA reductase. These agents include the natural fermentation products, such as mevastatin, lovastatin and pravastatin, and semisynthetic analogs, such as simvastatin. These compounds have the following chemical structural formulae:

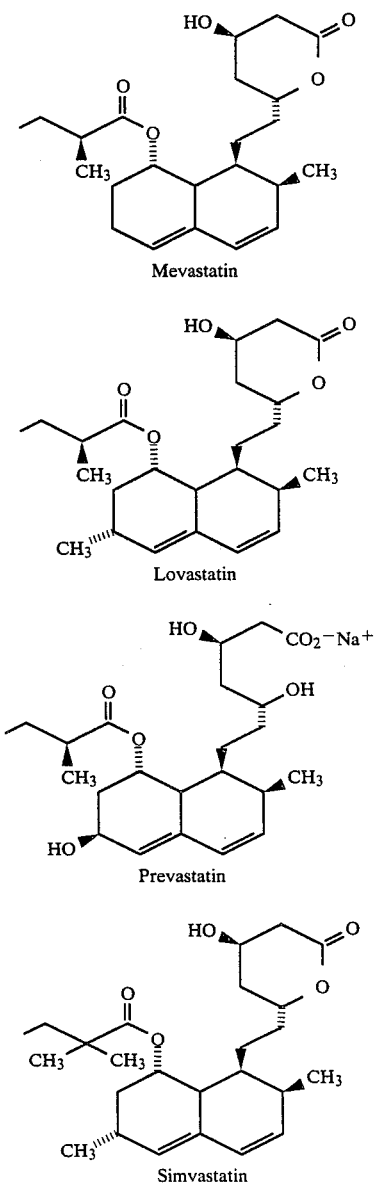

Mevastatin

Lovastatin

Prevastatin

Simvastatin

Recently, MEVACOR®, which contains lovastatin as the active agent, was approved by the Food and Drug Administration for use as an antihypercholesterolemic drug.

Numerous analogs and homologs of these compounds have been described in the patent literature. U.S. Pat. No. 4,444,784 discloses analogs of lovastatin which possess polyhydronaphthyl moieties and various 8-acyloxy groups attached thereto. U.S. Pat. No. 4,661,483 also discloses analogs of lovastatin wherein the 8-acyloxy group has been elaborated. Additionally, co-pending U.S. applications Ser. Nos. 859,513, 859,524, 859,525, 859,530, 859,534, and 859,535 all filed on May 5, 1986, disclose further analogs of lovastatin which have functionalized 8-acyloxy groups. All Of the lovastatin analogs, including simvastatin, which contain a 6-methyl group have that substituent in the natural 6α (axial) configuration.

Co-pending U.S. patent application, Ser. No. 048,136 filed May 15, 1987, discloses compounds which are analogs of lovastatin and related compounds which possess a hydroxymethyl group, acyloxymethyl group, carbamoyloxymethyl group, a carboxy group, an alkoxycarbonyl group or a carbamoyl group substituted on the 6-position of the polyhydronaphthyl moiety. The compounds in this application may possess a substituent in the 6-position in either the 6α or 6β stereochemical position.

Co-pending U.S. patent application, Ser. No. 092,354 filed Sept. 2, 1987, discloses compounds which are analogs of lovastatin and related compounds which possess a methyl group in the 6-position in the 6β stereochemical position.

Co-pending U.S. patent application, Attorney Docket No. 17703, filed contemporaneously herewith, discloses compounds which are analogs of lovastatin and related compounds which contain gemdisubstitution at the 6,6 positions of the polyhydronaphthyl moiety.

Co-pending U.S. patent application, Attorney Docket No. 17706, filed contemporaneously herewith, discloses compounds which are analogs of lovastatin and related compounds which contain two double bonds in the 4,4a- and 5,6- positions or one double bond in the 5,6- position of the polyhydronaphthyl moiety.

SUMMARY OF THE INVENTION

This invention relates to novel compounds which are HMG-CoA reductase inhibitors and are useful as antihypercholesterolemic agents. Specifically, the compounds of this invention are analogs of lovastatin and related compounds which possess an aminoalkyl group, or sustituted aminoalkyl group, on the 6-position of the polyhydronaphthyl moiety. Additionally, pharmaceutical compositions of these novel compounds, as the sole therapeutically active ingredient and in combination with bile acid sequestrants, are disclosed. Other embodiments of this invention are methods of treating disease conditions in which hypercholesterolemia is an etiological factor, and processes for preparing the novel compounds.

DETAILED DESCRIPTION OF THE INVENTION

The specific HMG-CoA reductase inhibitors of this invention are the compounds represented by the following general structural formulae (I) and (II):

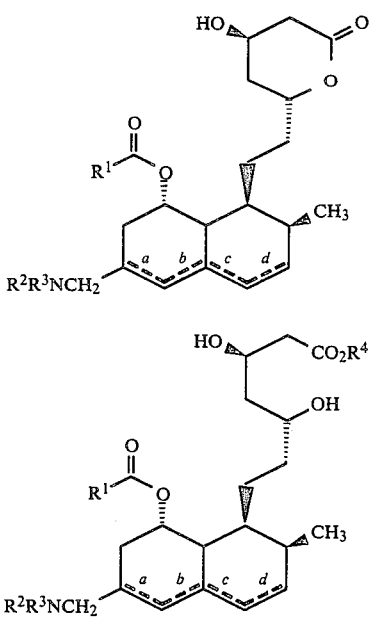

wherein:

R¹ is selected from:
(1) $C_{1-10}$ alkyl;
(2) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS$(O)_n$ in which n is 0 to 2,
 (j) $C_{3-8}$ cycloalkyl$(O)_n$,
 (k) phenylS$(O)_n$,
 (l) substituted phenylS$(O)_n$ in which the substituents are X and Y, and
 (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
 (a) $C_{1-10}$ alkyl
 (b) substituted $C_{1-10}$ alkyl in which the substituent is selected from
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy
  (vi) phenyl,
  (vii) substituted phenyl in which the substituents are X and Y
  (viii) $C_{1-10}$ alkylS$(O)_n$,
  (ix) $C_{3-8}$ cycloalkylS$(O)_n$,
  (x) phenylS$(O)_n$,
  (xi) substituted phenylS$(O)_n$ in which the substituents are X and Y, and
  (xii) oxo,
 (c) $C_{1-10}$ alkylS$(O)_n$
 (d) $C_{3-8}$ cycloalkylS$(O)_n$,
 (e) phenylS$(O)_n$,
 (f) substituted phenylS$(O)_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
 (a) piperidinyl,
 (b) pyrrolidinyl,
 (c) piperazinyl,
 (d) morpholinyl, and
 (e) thiomorpholinyl; and
(17) $R^6S$ in which $R^6$ is selected from
 (a) $C_{1-10}$ alkyl,
 (b) phenyl, and
 (c) substituted phenyl in which the substituents are X and Y;

$R^2$ and $R^3$ are independently selected from:
(1) hydrogen;
(2) $C_{1-10}$ alkyl;
(3) substituted $C_{1-10}$ alkyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(4) $C_{1-10}$ acyl;
(5) substituted $C_{1-10}$ acyl in which one or more substituent(s) is selected from
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y, and
 (i) oxo;
(6) phenylcarbonyl;
(7) substituted phenylcarbonyl in which the substituents are X and Y;
(8) $C_{1-5}$ alkylaminocarbonyl;

(9) di($C_{1-5}$ alkyl)aminocarbonyl;
(10) phenylaminocarbonyl;
(10) substituted phenylaminocarbonyl in which the substituents are X and Y;
(11) phenyl $C_{1-10}$ alkylaminocarbonyl;
(12) substituted phenyl $C_{1-10}$ alkylaminocarbonyl in which the substituents are X and Y;

$R^4$ is selected from:
(1) hydrogen;
(2) $C_{1-5}$ alkyl;
(3) substituted $C_{1-5}$ alkyl in which the substituent is selected from
  (a) phenyl,
  (b) dimethylamino, and
  (c) acetylamino, and
(4) 2,3-dihydroxypropyl;

X and Y independently are hydrogen, halogen, trifluoromethyl, $C_{1-3}$ alkyl, nitro, cyano or group selected from:
(1) $R^8O(CH_2)_m$ in which m is 0 to 3 and $R^8$ is hydrogen, $C_{1-3}$ alkyl or hydroxy-$C_{2-3}$alkyl;
(2)

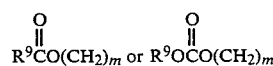

$$R^9\overset{O}{\overset{\|}{C}}O(CH_2)_m \text{ or } R^9O\overset{O}{\overset{\|}{C}}O(CH_2)_m$$

in which $R^9$ is hydrogen, $C_{1-3}$alkyl, hydroxy-$C_{2-3}$alkyl, phenyl, naphthyl, amino-$C_{1-3}$alkyl, $C_{1-3}$alkylamino-$C_{1-3}$alkyl, di($C_{1-3}$alkyl)amino-$C_{1-3}$alkyl, hydroxy-$C_{2-3}$alkylamino-$C_{1-3}$alkyl or di(hydroxy-$C_{2-3}$alkyl; amino-$C_{1-3}$alkyl;
(3)

$$R^{10}O\overset{O}{\overset{\|}{C}}(CH_2)_m$$

in which $R^{10}$ is hydrogen, $C_{1-3}$alkyl, hydroxy-$C_{2-3}$ alkyl, $C_{1-3}$alkoxy-$C_{1-3}$alkyl, phenyl or naphthyl;
(4)

$$R^{11}R^{12}N(CH_2)_m, R^{11}R^{12}N\overset{O}{\overset{\|}{C}}(CH_2)_m \text{ or } R^{11}R^{12}NC\overset{O}{\overset{\|}{O}}(CH_2)_m$$

in which $R^{11}$ and $R^{12}$ independently are hydrogen, $C_{1-3}$ alkyl, hydroxy-$C_{2-3}$ alkyl or together with the nitrogen atom to which they are attached form a heterocyclic group selected from piperidinyl, pyrrolidinyl, piperazinyl, morpholinyl or thiomorpholinyl;
(5) $R^{13}S(O)_n(CH_2)_m$ in which $R^{13}$ is hydrogen, $C_{1-3}$alkyl, amino, $C_{1-3}$alkylamino or di($C_{1-3}$alkyl)amino; and a, b, c and d each represent single bonds or one of a, b, c and d represents a double bond or both a and c or b and d represent double bonds;

or a pharmaceutically acceptable salt thereof.

Except where specifically defined to the contrary, the terms "alkyl", "alkoxy" and "acyl" include both the straight-chain and branched-chain species of the term.

One embodiment of this invention is the class of compounds of the formulae (I) and (II) wherein: $R^1$ is selected from
(1) $C_{1-10}$ alkyl;
(2) substituted $C_{1-10}$ alkyl in which one or more substituent(s) is selected from
  (a) halogen,
  (b) hydroxy,
  (C) $C_{1-10}$ alkoxy,
  (d) $C_{1-5}$ alkoxycarbonyl,
  (e) $C_{1-5}$ acyloxy,
  (f) $C_{3-8}$ cycloalkyl,
  (g) phenyl,
  (h) substituted phenyl in which the substituents are X and Y, and
  (i) oxo;
(3) $C_{3-8}$ cycloalkyl;
(4) Substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl,
    (vii) subsituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ acyloxy,
  (h) phenyl,
  (i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

More specifically illustrating this embodiment are the compounds wherein:
$R^1$ is selected from:
(1) $C_{1-10}$ alkyl;
(2) $C_{3-8}$ cycloalkyl;
(3) phenylamino; and
(4) substituted phenylamino in which the substituents are X and Y.

One subclass of this embodiment is the compounds of the formulae (I) and (II) wherein: $R^2$ and $R^3$ are hydrogen.

Exemplifying this subclass are those compounds of the formulae (I) and(II) wherein both b and d represent double bonds, especially the following compounds:
(1) 6(R)-[2-[8(S)-(2,2-dimethylbutyryloxy)-2(S)-methyl-6(S)-aminomethyl-1,2,6,7,8,8a(R)-hexahydronaphthyl-1(S)]ethyl]-4(R)-hydroxy-3,4,5,6-tetrahydro-2H-pyran-2-one;
(2) 6(R)-[2-[8(S)-(2,2-dimethylbutyryloxy)-2(S)-methyl-6(R)-aminomethyl-1,2,6,7,8,8a(R)-hexahydronaphthyl-1(S)]ethyl]-4(R)-hydroxy-3,4,5,6-tetrahydro-2H-pyran-2-one;
(3) 6(R)-[2-[8(S)-(2-methylbutyryloxy)2(S)-methyl-6(S)-aminomethyl-1,2,6,7,8,8a(R)-hexa-hydronaphthyl-1(S)]ethyl]-4(R)-hydroxy-3,4,5,6-tetrahydro-2H-pyran-2-one; (4) 6(R)-[2-[8(S)-(2-methylbutyryloxy)

the corresponding ring opened dihydroxy acids, and esters thereof, particularly the methyl ester.

A second subclass of this embodiment is the compounds of the formulae (I) and (II) wherein: $R^2$ is $C_{1-1}$ alkyl or substituted $C_{1-10}$ alkyl and $R^3$ is hydrogen Exemplifying this subclass are those compounds of the formulae (I) and(II) wherein both b and d represent double bonds, especially the following compounds:

(1) 6(R)-[2-[8(S)-(2,2-dimethylbutyryloxy)-2(S)-methyl-6(S)-benzylaminomethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-benzylaminomethyl-1,2,6,7,8,8a(R)-hexahydronaphthyl-1(S)]ethyl]-4(R)-hydroxy-3,4,5,6tetrahydro-2H-pyran-2-one;

(3) 6(R)-[2-[8(S)-(2-methylbutyryloxy)-2(S)-methyl-6(S)-benzylaminomethyl-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-benzylaminomethyl-1,2,6,7,8,8a(R)-hexahydronaphthyl-1(S)]ethyl]-4(R)-hydroxy-3,4,5,6-tetrahydro-2H-pyran-2-one; and the corresponding ring opened dihydroxy acids, and esters thereof, particularly the methyl ester.

A third subclass of this embodiment is the compounds of the formulae (I) and (II) wherein: $R^2$ is phenylcarbonyl or substituted phenylcarbonyl and $R^3$ is hydrogen.

Exemplifying this subclass are those compounds of the formulae (I) and(II) wherein both b and d represent double bonds, especially the following compounds:

(1) 6(R)-[2-[8(S)-(2,2-dimethylbutyryloxy)-2(S)-methyl-6(S)-phenylcarbonylaminomethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-phenylcarbonylaminomethyl-1,2,6,7,8,8a(R)-hexahydronapthyl-1(S)]ethyl]-4(R)-hydroxy-3,4,5,6-tetrahydro-2H-pyran-2-one;

(3) 6(R)-[2-[8(S)-(2-methylbutyryloxy)-2(S)-methyl-6(S)-phenylcarbonylaminomethyl-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-phenylcarbonylaminomethyl-1,2,6,7,8,8a(R)-hexahydronaphthyl-1(S)]ethyl]-4(R)-hydroxy-3,4,5,6-tetrahydro-2H-pyran-2-one; and the corresponding ring opened dihydroxy acids, and esters thereof, particularly the methyl ester.

A fourth subclass of this embodiment is the compounds of the formulae (I) and (II) wherein: $R^2$ is phenylaminocarbonyl or substituted phenylaminocarbonyl and $R^3$ is hydrogen.

Exemplifying tiis subclass are those compounds of the formulae (I) and (II) wherein both b and d represent double bonds, especially the following compounds:

(1) 6(R)-[2-[8(S)-(2,2-dimethylbutyryloxy) -2(S)-methyl-6(S)-phenylureidomethyl-1,2,6,7,8,8a(R)hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-phenylureidomethyl-1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-(2-methylbutyryloxy)-2(S)-methyl-6(S)-phenylureidomethyl-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(2-methylbutyryloxy)-2(S)-methyl-6(R)-phenylureidomethyl-1,2,6,7,8,8a(R)-hexahydro naphthyl-1(S)]ethyl]-4(R)-hydroxy-3,4,5,6-tetrahydro-2H-pyran-2-one; and the corresponding ring opened dihydroxy acids, and esters thereof, particularly the methyl ester.

A fifth subclass of this embodiment is the compounds of the formulae (I) and (II) wherein: $R^2$ is phenyl $C_{1-10}$ alylaminocarbonyl or substituted phenyl $C_{1-10}$ alkylaminocarbonyl and $R^3$ is hydrogen.

Exemplifying this subclass are those compounds of the formulae (I) and(II) wherein both b and d represent double bonds, especially the following compounds:

(1) 6(R)-[2-[8(S)-(2,2-dimethylbutyryloxy)-2(S)-methyl-6(S)-benzylureidomethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethylbutyryloxy)-2(S)-methyl-6(R)-benzylureidomethyl-1,2,6,7,8,8,a(R)-hexahydronaphthyl-1(S)]ethyl]-4(R)-hydroxy-3,4,5,6-tetrahydro-2H-pyran-2-one;

(3) 6(R)-[2-[8(S)-(2-methylbutyryloxy)-2(S)-methyl-6(S)-benzylureidomethyl-1,2,6,7,8,8a(R)-hexahydronaphthyl-1(S)]ethyl]-4(R)-hydroxy-3,4,5,6-tetrahydro-2H-Pyran-2-one;

(4) 6(R)-[2-[8(S)-(2-methylbutyryloxy)-2(S)-methyl-6(R)-benzylureidomethyl-1,2,6,7,8,8a(R)-hexahydronaphthyl-1(S)]ethyl]-4(R)-hydroxy-3,4,5,6-tetrahydro-2H-pyran-2-one; and the corresponding ring opened dihydroxy acids, and esters thereof, particularly the methyl ester.

The compounds of formulae (I) and (II) are conveniently prepared without inverting the absolute stereochemical configuration at the 6- position of the polyhydronaphthyl moiety from the corresponding 6(R)-[2-[8(S)-(acyloxy)-2(S)-methyl-6-hydroxymethylpolyhydro-naphthyl1(S)]ethyl]-4(R)-hydroxy-3,4,5,6-tetrahydro-2H-Pyran-2-one via the following synthetic pathway:

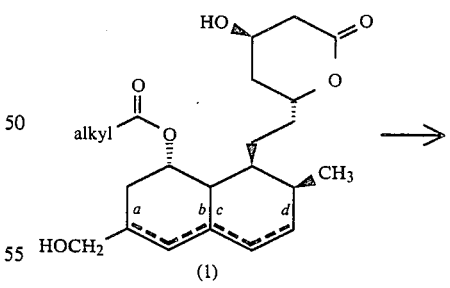

(1)

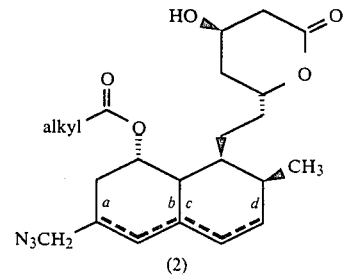

(2)

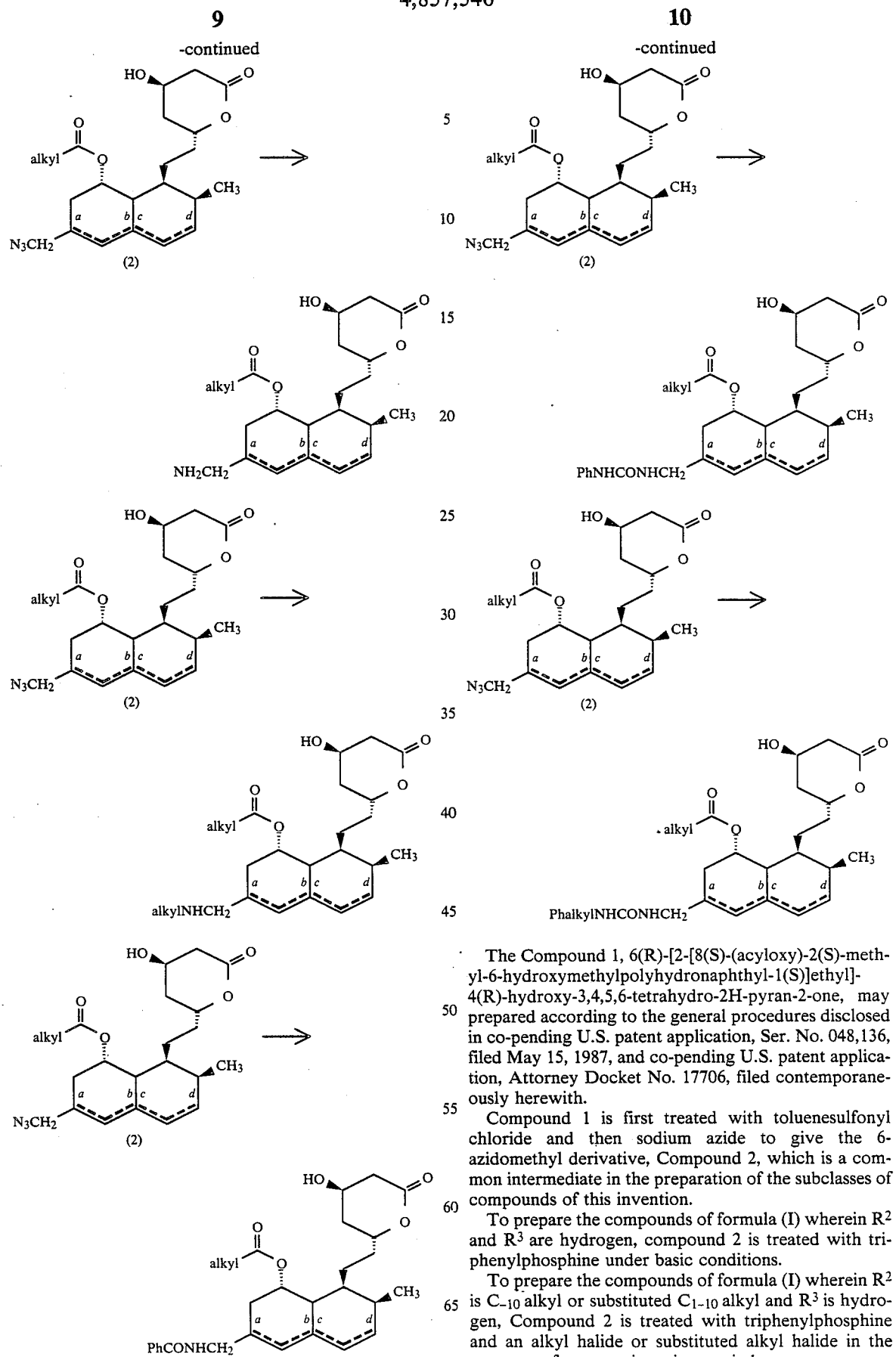

The Compound 1, 6(R)-[2-[8(S)-(acyloxy)-2(S)-methyl-6-hydroxymethylpolyhydronaphthyl-1(S)]ethyl]-4(R)-hydroxy-3,4,5,6-tetrahydro-2H-pyran-2-one, may prepared according to the general procedures disclosed in co-pending U.S. patent application, Ser. No. 048,136, filed May 15, 1987, and co-pending U.S. patent application, Attorney Docket No. 17706, filed contemporaneously herewith.

Compound 1 is first treated with toluenesulfonyl chloride and then sodium azide to give the 6-azidomethyl derivative, Compound 2, which is a common intermediate in the preparation of the subclasses of compounds of this invention.

To prepare the compounds of formula (I) wherein $R^2$ and $R^3$ are hydrogen, compound 2 is treated with triphenylphosphine under basic conditions.

To prepare the compounds of formula (I) wherein $R^2$ is $C_{-10}$ alkyl or substituted $C_{1-10}$ alkyl and $R^3$ is hydrogen, Compound 2 is treated with triphenylphosphine and an alkyl halide or substituted alkyl halide in the presence of an organic or inorganic base.

To prepare the compounds of formula (I) wherein $R^2$ is phenylcarbonyl or substituted phenylcarbonyl and $R^3$ is hydrogen, Compound 2 is treated with triphenylphosphine and phenylacetyl halide or substituted phenylacetyl halide in the presence of an organic base.

To prepare the compounds of formula (I) wherein $R^2$ is phenylaminocarbonyl or substituted phenylaminocarbonyl and $R^3$ is hydrogen, Compound 2 is treated with triphenylphosphine and phenylisocyanate or substituted phenylisocyanate.

To prepare the compounds of formula (I) wherein $R^2$ is phenyl $C_{1-10}$ alkylaminocarbonyl or substituted phenyl $C_{1-10}$ alkylaminocarbonyl and $R^3$ is hydrogen, Compound 2 is treated with triphenylphosphine and phenyl $C_{1-10}$ alkylisocyanate or substituted phenyl $C_{1-10}$ alkylisocyanate.

To prepare the compounds of formula (I) wherein $R^2$ and $R^3$ are other than hydrogen, Compound 2 is first treated with triphenylphosphine, alkylated or acylated as described above and then treated with a second agent to introduce the second substituent.

Where the product formed by the above described synthetic pathways is not the desired form of that compound, then that product may be subjected to one or more further reactions such as hydrolysis, salification, esterification, acylation, ammonolysis or lactonization by conventional methods, as described in more detail hereafter.

The starting compound may be a free carboxylic acid, its corresponding lactone or a salt (e.g., metal, amino acid or amine salt) or ester particularly alkyl ester) thereof.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, histidine, $\alpha,\beta$-diaminobutyric acid or ornithine.

Preferred amines to form amine salts include t-octylamine, dibenzylamine, dichlorohexylamine, morpholine, alkyl esters of D-phenylglycine and D-glucosamine. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenyl $C_{1-5}$alkyl, dimethylamino-$C_{1-5}$alkyl, or acetylamino-$C_{1-5}$alkyl may be employed if desired.

Of the starting materials, the alkali metal salts, e.g., the sodium or potassium salts, are particularly preferred, the sodium salt being most preferred as it has been found that this gives the best conversion of the substrate into the desired product.

Where the product obtained by the processes of the present invention is a salt of the carboxylic acid of formula (II), the free carboxylic acid itself can be obtained by adjusting the pH of the filtrate to a value of 4 or less, preferably to a value of from 3 to 4. Any organic acid or mineral acid may be employed, provided that it has no adverse effect upon the desired compound. Examples of the many acids which are suitable include trifluoroacetic acid, acetic acid, hydrochloric acid and sulphuric acid. This carboxylic acid may itself be the desired product or it may be, and preferably is, subjected to subsequent reactions, as described below, optionally after such treatments as extraction, washing and lactonization.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic ether (such as THF) or an ester (such as ethyl acetate). It is preferred to use a mixture of a hydrophilic organic solvent with water. Such reactions are normally conducted at ambient temperature but they may, if desired, be conducted with heating.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by a salt exchange reaction.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction; suitable solvents include benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. All of the reactions for producing esters are preferably effected at about ambient temperature, but, if required by the nature of the reaction system, the reactions may be conducted with heating.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.* 28, p. 347-358 (1985).

For estimation of relative inhibitory potencies, mevastatin (compactin) was assigned a value of 100 and the $IC_{50}$ value of the test compound was compared with that of compactin determined simultaneously in the published in vitro protocol.

Representative of the intrinsic HMG-CoA reductase inhibitory activities of the claimed compounds are the relative potencies tabulated below for a number of the claimed compounds.

| R | $R^1$ | Relative Potency |
| --- | --- | --- |
| H | 1,1-dimethylpropyl | 125 |
| PhCH₂ | 1,1-dimethylpropyl | 167 |
| PhCO | 1,1-dimethylpropyl | 300 |
| PhNHCO | 1,1-dimethylpropyl | 294 |
| PhCH₂NHCO | 1,1-dimethylpropyl | 500 |

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminoPropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(2,2-dimethylbutyryloxy)-2(S)-methyl-6(S)-aminomethyl-1,2,6,7,8,8a(R)-hexahydronaphthyl-1(S)]ethyl]-4(R)-hydroxy-3,4,5,6-tetrahydro-2H-pyran-2one (a)
6(R)-[2-[8(S)-(2,2-dimethylbutyryloxy)-2(S)-methyl-6(S)-p-toluenesulfonyloxymethyl-1,2,6,7,8,8a(R)-hexahydronaphthyl-1(S)]ethyl]-4(R)-hydroxy-3,4,5,6-tetrahydro-2H-pyran-2-one (1a)

To a stirred solution of 6(R)-[2-[8(S)-(2,2-dimethylbutyryloxy)-2(S)-methyl-6(S)-hydroxymethyl-1,2,6,7,8,8a(R)-hexahydronaphthyl-1(S)]ethyl]-4(R)-hydroxy-3,4,5,6-tetrahydro-2H-pyran-2-one (0.50 g, 1.1 mmol) and pyridine (0.37 ml, 4.6 mmol) in methylene chloride (2.3 ml) at 25° C. was added p-toluenesulfonyl chloride (0.24 g, 1.3 mmol). After about 20 hours, the reaction mixture was diluted with ethyl acetate, washed with water and brine, dried over MgSO₄ and concentrated. Flash chromatography (silica, 50 to 75 percent ethyl acetate in hexane) gave the desired compound as a colorless oil.

$^1$H NMR (CDCl₃) δ 7.76 (d,2H,J=7 Hz), 7.35 (d,2H,J=7 Hz), 5.90 (d,1H,J=8 Hz), 5.80 (dd,1H,J=8 and 5 Hz), 5.28 (s, 2H), 4.59 (m,1H), 4.35 (m,1H), 3.90 (d,2H,J=6 Hz), 2.80-1.10 (m), 2.43 (s,3H), 1.10 (s,3H), 0.88 (d,3H,J=Hz), 0.78 (t,3H,J=7 Hz).

(b) 6(R)-[2-[8(S)-(2,2-dimethylbutyryloxy)-2(S)-methyl 6(S)-azidomethyl-1,2,6,7,8,8a(R)-hexahydronaphthyl-1(S)]ethyl]-4(R)-hydroxy-3,4,5,6-tetrahydro-2H-pyran-2-one (1b)

To a stirred solution of the compound 1a (1.4 g, 2.4 mmol) in dry dimethylsulfoxide (8.2 ml) was added sodium azide (0.66 g, 9.9 mmol) at 25° C. After stirring for about 48 hours, the green reaction mixture was diluted with ethyl acetate, washed with water, and brine, dried over MgSO₄ and concentrated. Flash chromatogrphy (silica, 50 percent ethyl acetate in hexane) afforded the desired compound as an amorphorous solid.

$^1$H NMR (CDCl₃) δ 5.97 (d, b 1H, J=8 Hz), 5.82 (dd, 1H, J=8 and 5 Hz), 5.44 (s, 1H), 5.35 (m, 1H), 4.60 (m,1H), 4.37 (m, 1H), 3.28 (m,2H), 2.78-1.25 (m), 1.12 (s, 6H), 0.89 (d, 3H, J=6 Hz), 0.82 (t, 3H,J=7 Hz).

Elemental Anal. C₂₅H₃₇O₅N₃:
Calc'd: C, 65.31; H, 8.14; N, 9.14. Found: C, 65.71; H, 8.21; N, 8.75.

(c)
7-[1,2,6,7,8,8a(R)-hexahydro-2(S)-methyl-6(S)-aminomethyl-8(S)-(2,2-dimethylbutyryloxy)-naphthalenyl-1 (S)]-3(R), 5(R)-dihydroxyheptanoic acid sodium salt 8(S)-(2,2-dimethylbutyryloxy)-naphthalenyl- To a stirred solution of the compound 1(71 mg, 0.15 mmol) in tetrahydrofuran (0.77 ml) at 25° C. was added 1 N sodium hydroxide (155 μl, 0.15 ml). After 15 minutes, triphenylphosphine (0.16 g, 0.62 mmol) was added and the reaction mixture stirred for about 16 hours. The reaction mixture was then diluted with water, washed with diethyl ether, and concentrated. The residue was purified by chromatography (XAD-4 resin, 20-40 percent acetonitrile in water) to afford the desired compound which is the sodium salt of 6(R)-[2-[8(S)-(2,2-dimethylbutyryloxy)-2(S)-methyl-6(S)-aminomethyl- 1,2,6,7,8,8a(R)-hexahydronaphthyl-1(S)]ethyl]-4(R)-hydroxy-3,4,5,6-tetrahydro-2H-pyran-2-one as a beige solid (mp 150° C. dec.). $^1$H NMR (CD$_3$OD) δ 6.02 (d, 1H, J=8 Hz), 5.86 (dd, 1H, J=8 and 5 Hz), 5.50 (m, 1H), 5.35 (m, 1H), 4.09 (m, 1H), 3.82 (m, 1H) 2.78 (d, 2H, J=6 Hz), 2.50-2.20 (m,3H), 1.80-1.20 (m), 1.15 (s, 6H) 0.93 (d, 3H, J=7 Hz), 0.88 (t, 3H, J=7 Hz).

Elemental Anal. C$_{25}$H$_{40}$O$_6$NNa·0.5 H$_2$O:
Calc'd: C, 62.20; H, 8.59;NN, 2.90. Found: C, 61.85; H, 8.39; N, 2.77.

EXAMPLE 2

Preparation of
6(R)-[2-[8(S)-(2,2-dimethylbutyryloxy)-2(S)-methyl-6(S)-benzylaminomethyl-1,2,6,7,8,8a(R)-hexahydronaphthyl-1(S)]ethyl]-4(R)-hydroxy-3,4,5, 6-tetrahydro-2H-pyran-2-one A mixture of the compound 1b (0.10 g, 0.22 mmol), and triphenylphosphine (0.11 g, 0.44 mmol) in THF (1.8 ml) and water (100 μl) was stirred at 25° C. for about 16 hours. The mixture was then treated with benzyl bromide (28 μl, 0.24 mmol). After about 4 hours, the reaction mixture was diluted with acetic acid (50 μl) and water (1.0 ml) and washed with ethyl acetate (2x). The aqueous phase was cooled to about 0° C. in an ice bath and treated with an excess Of sodium bicarbonate and then extracted with ethyl acetate (2x). The comined organic extracts were dried over MgSO$_4$ and concentrated. The residue was flash chromatographed (silica, ethyl acetate with 1 percent triethylamine) to yield the desired compound. The compound was dissolved in diethyl ether and treated with a saturated hydrochloric acid/diethyl ether solution to precipitate the hydrochloride salt as a white solid (mp 222°-234° C. dec.)

$^1$H NMR (CD$_3$OD) δ 7.50 (m, 5H), 6.04 (d, 1H, J=8 Hz), 5.90 (dd, 1H, J=8 and 5 Hz), 5.45 (bs, 1H), 5.35 (bs, 1H), 4.63 (m, 1H) 4.30 (m, 1H), 3.08 (m, 2 H), 2.72 (m, 2H), 2.57-2.25 (m, 4H), 1.95-1.30 (m), 1.15 (s, 6H), 0.94 (d, 3H, J=6 Hz), 0.87 (t, 3H, J=7 Hz).

Elemental Anal. C$_{32}$H$_{46}$ClNO$_5$: Calc'd: C, 68.61; H, 8.28; N, 2.50. Found: C, 68.24; H, 8.22; N, 2.52.

EXAMPLE 3

Preparation of
6(R)-[2-[8(S)-(2,2-dimethylbutyryloxy)-2(S)-methyl-6(S)-phenylcarbonylaminomethyl-1,2,6,7,8,8a(R)-hexahydronaphthyl-1(S)]ethyl]-4(R)-hydroxy-3,4,5,6-tetrahydro-2H-pyran-2-one To a stirred solution of the compound 1b (60 mg, 0.13 mmol), pyridine (32 μl, 0.39 mmol) and benzoyl chloride (45 μl, 0.39 mmol) in THF (0.66 ml) and water (5 μl) at 25° C. was added triphenylphosphine (0.17 g, 0.65 mmol). After about 6 hours, the reaction mixture was concentrated and the residue purified by flash chromatography (silica, 50 percent ethyl acetate in hexane) to give crude product. After a second flash chromatography (silica, 10 percent acetone in methylene chloride), the desired compound was obtained as a colorless solid (mp 118°-120° C.)

$^1$H NMR (CDCl$_3$) δ 7.77 (d, 2H, J=8 Hz), 7.48 (m, 3H) 6.27 (m, 1H) 6.02 (d, 1H, J=8 Hz), 5.85 (dd, 1H, J=8 and 5 Hz), 5.50 (bs, 1H), 5.38 (bs, 1H), 4.64 (m, 1H) 4.38 (m, 1H), 3.62 (m, 1H), 3.38 (m, 2H), 2.75-1.20 (m), 1.15 (s, 6H), 0.93 (d, 3H, J=6 Hz), 0.83 (t, 3H, J=7 Hz).

Elemental Anal. C$_{32}$H$_{43}$NO$_6$·0.5 H$_2$O: Calc'd: C, 70.28; H, 8.13; N, 2.56. Found: C, 70.02; H, 8.35; N, 2.51.

EXAMPLE 4

Preparation of
6(R)-[2-[8(S)-(2,2-dimethylbutyryloxy)-2(S)-methyl-6(S)-phenylureidomethyl-1,2,6,7,8,8a(R)-hexahydronaphthyl-1(S)]ethyl]-4(R)-hydroxy-3, 4,5,6-tetrahydro-2H-pyran-2-one To a stirred solution of the compound 1b (0.10 g, 0.22 mmol), in THF (1.1 ml) and water (8 μl) at 25° C. was added triphenylphosphine (0.29 g, 1.1 mmol). After about 1.5 hours, the reaction mixture was cooled to 0° C. in an ice bath and treated with phenylisocyante (26 μl, 0.24 mmol). After about 20 minutes, the reaction mixture was diluted with ethyl acetate, washed with water and brine, dried over MgSO$_4$ and concentrated. The residue was flash chromatographed (silica, 20 percent acetone in methylene chloride) to give the desired compound as a colorless amorphorous solid.

$^1$H NMR (CDCl$_3$) δ 7.26 (m, 5H) 5.95 (d, 1H, J=8 Hz), 5.76 (dd, 1H, J=8 and 5 Hz), 5.38 (bs, 1H), 5.30 (bs, 1H), 5.15 (m, 1H), 4.62 (m, 1H), 4.34 (m, 1H), 3.37 (m, 1H), 3.12 (m, 1H), 2.75-1.20 (m), 1.10 (s, 6H), 0.89 (d, 3H, J=7 Hz), 0.80 (t, 3H, J=8 Hz).

Elemental Anal C$_{32}$H$_{44}$N$_2$O$_6$·0.5 H$_2$O: Calc'd: C, 68.40; H, 8.23; N, 4.99. Found: C, 68.86; H, 8.07; N, 4.69

EXAMPLE 5

Preparation of
6(R)-[2-[8(S)-(2,2-dimethylbutyryloxy)-2(S)-methyl-6(S)-benzylureidomethyl-1,2,6,7,8,8a(R)-hexahydronaphthyl-1(S)]ethyl]-4(R)-hydroxy-3, 4,5,6-tetrahydro-2H-pyran-2-one Utilizing the general procedure of Example 4, the compound 1b (105 mg, 0.23 mmol) was converted into the desired compound which was an amorphorous solid. $^1$H NMR (CDCl$_3$) δ 7.30 (m, 5H), 5.95 (d, 1H, J=7 Hz), 5.79 (dd, 1H, J=7 and 5 Hz), 5.40 (bs, 1H), 5.30 (bs, 1H), 4.61 (m, 2H), 4.37 (d, 2H, J=5 Hz), 4.31 (m, 1H), 3.29 (m, 1H), 3.15 (m, 1H), 2.68-1.25 (m), 1.10 (s, 6H), 0.90 (d, 3H, J=6 Hz), 0.82 (t, 3H, J=7 Hz).

Elemental Anal. C$_{33}$H$_{46}$N$_2$O$_6$: Calc'd C, 69.91; H, 8.20; N, 4.95. Found C, 69.93; H, 8.39; N, 4.62.

EXAMPLES 6 TO 8

Utilizing the general procedures described in Examples 1 to 4, the following compounds are prepared from the appropriately substituted starting materials and reactants.

| Compound No. | R | R$^1$ | a | b | c | d |
|---|---|---|---|---|---|---|
| 6 | H | sec-butyl | sb | sb | sb | sb |
| 7 | PhCH$_2$ | sec-butyl | db | sb | db | sb |
| 8 | PhCO | sec-butyl | sb | db | sb | db |
| 9 | PhNHCO | sec-butyl | sb | db | sb | sb |
| 10 | PhCH$_2$NHCO | sec-butyl | db | sb | sb | sb | sb = single bond;
db = double bond

EXAMPLE 11

Preparation of Ammonium Salts of Compounds II

The lactone (1.0 mmol) from Example 1 is dissolved with stirring in 0.1 N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is

17 removed by filtration and the filtrate saturated with ammonia (gas) to give a gum which solidified to provide the ammonium salt.

EXAMPLE 12

Preparation of Alkali and Alkaline Earth Salts of Comoounds II

To a solution of 42 mg of lactone from Example 1 in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 13

Preparation of Ethylenediamine Salts of Compounds II

To a solution of 0.50 g of the ammonium salt from Example 11 in 10 ml of methanol is added 75 ml of ethylenediamine. The methanol is stripped off under vacuum to obtain the desired ethylenediamine salt.

EXAMPLE 14

Preparation of Tris(hydroxymethyl)aminomethane Salts of Compounds II

To a solution of 202 mg of the ammonium salt from Example 11 in 5 ml of methanol is added a solution of 60.5 mg of tris(hydroxymethyl) aminomethane in 5 ml of methanol. The solvent is removed in vacuo to afford the desired tris(hydroxymethyl)aminomethane salt.

EXAMPLE 15

Preparation of L-Lysine Salts of Compounds II

A solution of 0.001 mole of L-lysine and 0.0011 mole of the ammonium salt from Example 11 in 15 ml of 85% ethanol is concentrated to dryness in vacuo to give the desired L-lysine salt.

Similarly prepared are the L-arginine, L-ornithine, and N-methylglucamine salts.

EXAMPLE 16

Preparation of Tetramethylammonium Salts of Compounds II

A mixture of 68 mg of ammonium salt from Example 11 in 2 ml of methylene chloride and 0.08 ml of 24% tetramethylammonium hydroxide in methanol is diluted with ether to yield the desired tetramethylammonium salt.

EXAMPLE 17

Preparation of Methyl Esters of Compounds II

To a solution of 400 mg of lactone from Example 1 in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried (Na₂SO₄), filtered and evaporated in vacuo to yield the desired methyl ester.

In like manner, by the use of equivalent amounts of propanol, butanol, isobutanol, t-butanol, amylalcohol, isoamylalcohol, 2,2-dimethylaminoethanol, benzylalcohol, 2-acetamidoethanol and the like, the corresponding esters are obtained.

EXAMPLE 18

Preparation of Free Dihydroxy Acids

The sodium salt of the compound II from Example 10 is dissolved in 2 ml of ethanol-water (1:1; v:v) and added to 10 ml of 1N hydrochloric acid from which the dihydroxy acid is extracted with ethyl acetate. The organic extract is washed once with water, dried (Na₂SO₄), and evaporated in vacuo with a bath temperature not exceeding 30° C. The dihydroxy acid derivative slowly reverts to the corresponding, parent lactone on standing.

EXAMPLE 19

As a specific embodiment of a composition of this invention, 20 mg of lactone from Example 1 is formulated with sufficient finely divided lactose to provide a total amount of 580 to 590 mg to fill a size 0, hard-gelatin capsule.

What is claimed is:

1. A compound represented by the following structural formula (I):

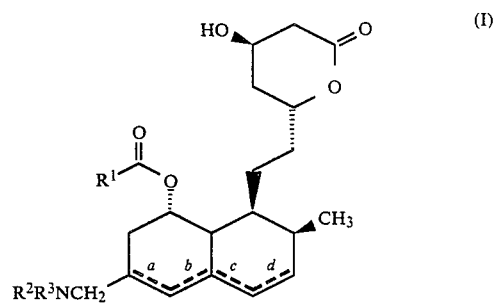

wherein:
R¹ is selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$ in which n is 0 to 2,
(j) $C_{3-8}$ cycloalkylS(O)$_n$,
(k) phenylS(O)$_n$,
(l) substituted phenylS(O)$_n$ in which the substituents are X and Y, and
(m) oxo;
(3) $C_{1-10}$ alkoxy;
(4) $C_{2-10}$ alkenyl;
(5) $C_{3-8}$ cycloalkyl;
(6) substituted $C_{3\alpha 8}$ cycloalkyl in which one substituent is selected from
(a) $C_{1-10}$ alkyl
(b) substituted $C_{1-10}$ alkyl in which the substituent is selected from
(i) halogen,
(ii) hydroxy,
(iii) $C_{1-10}$ alkoxy, (iv) C$_{1-5}$ alkoxycarbonyl,
(v) C$_{1-5}$ acyloxy,
(vi) phenyl,
(vii) substituted phenyl in which the substituents are X and Y,
(viii) C$_{1-10}$ alkylS(O)$_n$,
(ix) C$_{3-8}$ cycloalkylS(O)$_n$,
(x) phenylS(O)$_n$,
(xi) substituted phenylC(O)$_n$ in which the substituents are X and Y, and
(xii) oxo,
(c) C$_{1-10}$ alkylS(O)$_n$,
(d) C$_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) C$_{1-10}$ alkoxy,
(j) C$_{1-5}$ alkoxycarbonyl,
(k) C$_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) C$_{1-5}$ alkylamino;
(11) di(C$_{1-5}$ alkyl)amino;
(12) phenylamino;
(13) substituted phenylamino in which the substituents are X and Y;
(14) phenyl C$_{1-10}$ alkylamino;
(15) Substituted phenyl C$_{1-10}$ alkylamino in which the substituents are X and Y; and
(16) a member selected from
(a) C$_{1-10}$ alkyl,
(b) phenyl, and
(c) substituted phenyl in which the substituents are X and Y;
R$^2$ and R$^3$ are independently selected from:
(1) hydrogen;
(2) C$_{1-10}$ alkyl;
(3) substituted C$_{1-10}$ alkyl in which one or more substituent(s) is selected from
(a) halogen,
(b) hydroxy,
(c) C$_{1-10}$ alkoxy,
(d) C$_{1-5}$ alkoxycarbonyl,
(e) C$_{1-5}$ acyloxy,
(f) C$_{3-8}$ cycloalkyl,
(g) phenyl,
(h) substituted phenyl in which the substituents are X and Y, and
(i) oxo;
(4) C$_{1-10}$ acyl;
(5) substituted C$_{1-10}$ acyl in which one or more substituent(s) is selected from
(a) halogen,
(b) hydroxy,
(c) C$_{1-10}$ alkoxy,
(d) C$_{1-5}$ alkoxycarbonyl,
(e) C$_{1-5}$ acyloxy,
(f) C$_{3-8}$ cycloalkyl,
(g) phenyl,
(h) substituted phenyl in which the substituents are X and Y, and
(i) oxo;
(6) phenylcarbonyl;
(7) substituted phenylcarbonyl in which the substituents are X and Y;
(8) C$_{1-5}$ alkylaminocarbonyl;
(9) di(C$_{1-5}$alkyl)aminocarbonyl;
(10) phenylaminocarbonyl;
(10) substituted phenylaminocarbonyl in which the substituents are X and Y;
(11) phenyl C$_{1-10}$ alkylaminocarbonyl;
(12) substituted phenyl C$_{1-10}$ alkylaminocarbonyl in which the substituents are X and Y;
R$^4$ is selected from: trifluoromethyl, C$_{1-3}$ alkyl, nitro, cyano or group selected from:
(1) R$^8$O (CH$_2$) in which m is 0 to 3 and R$^8$ and hydrogen, C$_{1-3}$alkyl or hydroxy-C$_{2-3}$alkyl;
(2)

$$R^9\overset{O}{\underset{\|}{C}}O(CH_2)_m \text{ or } R^9O\overset{O}{\underset{\|}{C}}O(CH_2)_m$$

in which R$^9$ is hydrogen, C$_{1-3}$alkyl, hydroxy-C$_{2-3}$alkyl, phenyl, naphthyl, amino-C$_{1-3}$alkyl, C$_{1-3}$alkylamino-C$_{1-3}$alkyl, di(C$_{1-3}$alkyl)amino-C$_{1-3}$alkyl hydroxy-C$_{2-3}$alkylamino-C$_{1-3}$alkyl or di(hydroxy-C$_{2-3}$alkyl) amino-C$_{1-3}$alkyl;
(3)

$$R^{10}O\overset{O}{\underset{\|}{C}}(CH_2)_m$$

in which R$^{10}$ is hydrogen, C$_{1-3}$alkyl, hydroxy-C$_{2-3}$ alkyl, C$_{1-3}$alkoxy-C$_{1-3}$alkyl, phenyl or naphthyl;

$$R^{11}R^{12}N(CH_2)_m, R^{11}R^{12}N\overset{O}{\underset{\|}{C}}(CH_2)_m \text{ or } R^{11}R^{12}N\overset{O}{\underset{\|}{C}}O(CH_2)_m$$

in which R$^{11}$ and R$^{12}$ independently are hydrogen, C$_{1-3}$ alkyl or, hydroxy-C$_{2-3}$alkyl
(5) R$^{13}$S(O)$_n$(CH$_2$)$_m$ in which R$^{13}$ is hydrogen, C$_{1-3}$alkyl, amino, C$_{1-3}$alkylamino or di(C$_{1-3}$alkyl)amino; and
a, b, c and d each represent single bonds or one of a, b, c and d represents a double bond or both a and c or b and d represent double bonds;
or a pharmaceutically acceptable salt thereof.
2. A compound of claim 1 wherein: R$^1$ is selected from:
(1) C$_{1-10}$ alkyl;
(2) substituted C$_{1-10}$ alkyl in which one or more substituent(s) is selected from
(a) halogen,
(b) hydroxy;
(c) C$_{1-10}$ alkoxy,
(d) C$_{1-5}$ alkoxycarbonyl,
(e) C$_{1-5}$ acyloxy,
(f) C$_{3-8}$ cycloalkyl,
(g) phenyl,
(h) substituted phenyl in which the substituents are X and Y, and
(i) oxo;
(3) C$_{3-8}$ cYcloalkyl;
substituent C$_{3-8}$ is selected from substituent is selected from (a) $C_{1-10}$ alkyl,
(b) substituted $C_{1-10}$ alkyl in which the substituent is selected from
  (i) halogen,
  (ii) hydroxy,
  (iii) $C_{1-10}$ alkoxy
  (iv) $C_{1-5}$ acyloxy,
  (v) $C_{1-5}$ alkoxycarbonyl,
  (vi) phenyl,
  (vii) subsituted phenyl in which the substituents are X and Y, and
  (viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl $C_{1-10}$ alkylamino; and
(8) substituted phenyl $C_{1-10}$ alkylamino in which the substituents are X and Y.

3. A compound of claim 2 wherein: $R^1$ is selected from:
(1) $C_{1-10}$ alkyl;
(2) $C_{3-8}$ cycloalkyl;
(3) phenylamino; and
(4) substituted phenylamino in which the substituents are X and Y.

4. A compound of claim 3 wherein both b and d represent double bonds.

5. A compound of claim 4 wherein: $R^2$ and $R^3$ are hydrogen.

6. A Compound of claim 5 which is 6(R)-[2-[8(S)-(2,2-dimethylbutyryloxy)-2(S)-methyl-6(S)-aminomethyl-1,2,6,7,8,8a(R)-hexahydronaphthyl-1(S)]ethyl]-4(R)-hydroxy-3,4,5,6-tetrahydro-2H-pyran-2-One 7. A compound of claim 4 wherein: $R^2$ is $C_{1-10}$ alkyl or substituted $C_{1-10}$ alkyl and $R^3$ is hydrogen.

8. A compound of claim 7 which is 6(R)-[2-[8(S)-(2,2-dimethylbutyryloxy)-2(S)-methyl-6(S)-benzylaminomethyl-1,2,6,7,8,8a(R)-hexahydronaphthyl-1(S)]ethyl]-4(R)-hydroxy-3,4,5,6-tetrahydro-2H-pyran-2-one 9. A compound of claim 4 wherein: $R^2$ is phenylcarbonyl or substituted phenylcarbonyl and $R^3$ is hydrogen.

10. A compound of claim 9 which is 6(R)-[2-[8(S)-(2,2-dimethylbutyryloxy)-2(S)-methyl-6(S)-phenylcarbonylaminomethyl-1,2,6,7,8,8a(R)-hexahydronaphthyl-1(S)]ethyl]-4(R)-hydroxy-3,4,5,6-tetrahydro-2H-pyran-2-one 11. A compound of claim 4 wherein: $R^2$ is phenylaminocarbonyl or substituted phenylaminocarbonyl and $R^3$ is hydrogen.

12. A compound of claim 11 which is 6(R)-[2-[8(S)-(2,2-dimethylbutyryloxy)-2(S)-methyl-6(S)-phenylureidomethyl-1,2,6,7,8,8a(R)-hexahydronaphthyl1(S)]ethyl]-4(R)-hydroxy-3,4,5,6-tetrahydro-2H-pyran-2-one 13. A compound of claim 4 wherein: $R^2$ is phenyl $C_{1-10}$ alkylaminocarbonyl or substituted phenyl $C_{1-10}$ alkylaminocarbonyl.

14. A compound of claim 13 which is 6(R)-[2-[8(S)-(2,2-dimethylbutyryloxy)-2(S)-methyl-6(S)-benzylureidomethyl-1,2,6,7,8,8a(R)-hexahydronaphthyl1(S)ethyl]-4(R)-hydroxy-3,4,5,6-tetrahydro-2H-pyran-2-one 15. A hypocholesterolemic, hypolipidemic pharmaceutical composition comprising a pharmaceutically acceptable carrier and a nontoxic effective amount of a compound as defined in claim 1.

16. A composition of claim 15 in which the compound is selected from:
(1) 6(R)-[2-[8(S)-(2,2-dimethylbutyryloxy)-2(S)-methyl-6(S)-aminomethyl-1,2,6,7,8,8a(R)-hexahydronaphthyl-1(S)]ethyl]-4(R)-hydroxy-3,4,5,6-tetrahydro-2H-pyran-2-one;
(2) 6(R)-[2-[8(S)-(2,2-dimethylbutyryloxy)-2(S)-methyl-6(S)-benzylaminomethyl-1,2,6,7,8,8a(R)-hexahydronaphthyl-1(S)]ethyl]-4(R)-hydroxy-3,4,5,6-tetrahydro-2H-pyran-2-one;
(3) 6(R)-[2-[8(S)-(2,2-dimethylbutyryloxy)-2(S)-methyl-6(S)-phenylcarbonylaminomethyl-1,2,6,7,8, 8a(R)-hexahydronaphthyl-1(S)]ethyl]-4(R)-hydroxy-3,4,5,6-tetrahydro-2H-pyran-2-one;
(4) 6(R)-[2-[8(S)-(2,2-dimethylbutyryloxy)-2(S)-methyl-6(S)-phenylureidomethyl-1,2,6,7,8,8a(R)-hexahydronaphthyl-1(S)]ethyl]-4(R)-hydroxy-3,4,5,6-tetrahydro-2H-pyran-2-one;
(5) 6(R)-[2-[8(S)-(2,2-dimethylbutyryloxy)-2(S)-methyl-6(S)-benzylureidomethyl-1,2,6,7,8,8a(R)-hexahydronaphthyl-1(S)]ethyl]-4(R)-hydroxy-3,4,5,6-tetrahydro-2H-pyran-2-one 17. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

18. A method of inhibiting cholesterol biosynthesis comprising the administration to a subject in need of such treatment a nontoxic therapeutically effective amount of a compound of claim 1.

19. A method of claim 18 in which the compound is selected from:
(1) 6(R)-[2-[8(S)-(2,2-dimethylbutyryloxy)-2(S)-methyl-6(S)-aminomethyl-1,2,6,7,8,8a(R)-hexahydronaphthyl-1(S)]ethyl]-4(R)-hydroxy-3,4,5,6-tetrahydro-2H-pyran-2-one;
(2) 6(R)-[2-[8(S)-(2,2-dimethylbutyryloxy)-2(S)-methyl-6(S)-benzylaminomethyl-1,2,6,7,8,8a(R)-hexahydronaphthyl-1(S)]ethyl]-4(R)-hydroxy-34,5,6-tetrahydro-2H-pyran-2-one;
(3) 6(R)-[2-[8(S)-(2,2-dimethylbutyryloxy)-2(S)-methyl-6(S)-phenylcarbonylaminomethyl-1,2,6,7,8, 8a(R)-hexahydronaphthyl-1(S)]ethyl]-4(R)-hydroxy-3,4,5,6-tetrahydro-2H-pyran-2-one;
(4) 6(R)-[2-[8(S)-(2,2-dimethylbutyryloxy)-2(S)-methyl-6(S)-phenylureidomethyl-1,2,6,7,8,8a(R)-hexahydronaphthyl-1(S)]ethyl]-4(R)-hydroxy-3,4,5,6-tetrahydro-2H-pyran-2-one;
(5) 6(R)-[2-[8(S)-(2,2-dimethylbutyryloxy)-2(S)-methyl-6(S)-benzylureidomethyl-1,2,6,7,8,8a(R)-hexahydronaphthyl-1(S)]ethyl]-4(R)-hydroxy-3,4,5,6-tetrahydro-2H-pyran-2-one

* * * * *

UNITED STATES PATENT AND TRADEMARK OFFICE
CERTIFICATE OF CORRECTION

PATENT NO. : 4,857,546

DATED : August 15, 1989

INVENTOR(S) : M. Duggan et al

It is certified that error appears in the above-identified patent and that said Letters Patent is hereby corrected as shown below:

At column 19, line 37, delete "a member selected from" and insert therefor -- $R^6S$ in which $R^6$ is selected from --.

At column 20, line 13, delete "$R^4$ is selected from" and insert therefor -- X and Y independently are hydrogen, halogen, --.

At column 20, lines 66-68 should read --(3) $C_{3-8}$ cycloalkyl;
(4) substituted $C_{3-8}$ cycloalkyl in which one substituent is selected from--.

Signed and Sealed this

Fourth Day of September, 1990

*Attest:*

HARRY F. MANBECK, JR.

*Attesting Officer*     *Commissioner of Patents and Trademarks*